(12) United States Patent
Phillips et al.

(10) Patent No.: US 10,751,444 B2
(45) Date of Patent: Aug. 25, 2020

(54) FLOWABLE HEMOSTATIC GEL COMPOSITION AND ITS METHODS OF USE

(71) Applicant: Victor Matthew Phillips, Jefferson City, MO (US)

(72) Inventors: Victor Matthew Phillips, Jefferson City, MO (US); John Garner, West Lafayette, IN (US)

(73) Assignee: Victor Matthew Phillips, Jefferson City, MO (US)

( * ) Notice: Subject to any disclaimer, the term of this patent is extended or adjusted under 35 U.S.C. 154(b) by 373 days.

(21) Appl. No.: 14/820,936

(22) Filed: Aug. 7, 2015

(65) Prior Publication Data
US 2017/0035929 A1 Feb. 9, 2017

(51) Int. Cl.
*A61L 24/08* (2006.01)
*A61L 26/00* (2006.01)
*A61L 24/00* (2006.01)
*A61L 24/10* (2006.01)

(52) U.S. Cl.
CPC ........... *A61L 24/08* (2013.01); *A61L 24/0031* (2013.01); *A61L 24/106* (2013.01); *A61L 24/108* (2013.01); *A61L 26/008* (2013.01); *A61L 26/0023* (2013.01); *A61L 26/0066* (2013.01); *A61L 2300/418* (2013.01); *A61L 2400/04* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 5,510,102 | A | 4/1996 | Cochrum |
| 5,578,661 | A | 11/1996 | Fox et al. |
| 6,162,241 | A | 12/2000 | Coury et al. |
| 6,706,690 | B2 | 3/2004 | Reich et al. |
| 8,512,729 | B2 | 8/2013 | Wallace et al. |
| 8,603,511 | B2 | 12/2013 | Wallace et al. |
| 8,642,831 | B2 | 2/2014 | Larsen et al. |
| 8,703,170 | B2 | 4/2014 | Hedrich et al. |
| 8,940,335 | B2 | 1/2015 | Goessl |
| 8,999,376 | B2 | 4/2015 | Ericson |
| 9,017,664 | B2 | 4/2015 | Preiss-Bloom et al. |
| 9,662,400 | B2 * | 5/2017 | Smith ............. A61K 9/19 |
| 2002/0042378 | A1 | 4/2002 | Reich et al. |
| 2002/0131933 | A1 | 9/2002 | Delmotte |
| 2002/0193448 | A1 | 12/2002 | Wallace et al. |
| 2004/0136977 | A1 | 7/2004 | Miyamoto et al. |
| 2004/0214770 | A1 | 10/2004 | Reich et al. |
| 2005/0004158 | A1 | 1/2005 | Iyer et al. |
| 2005/0058688 | A1 | 3/2005 | Boerger et al. |
| 2005/0281873 | A1 | 12/2005 | Badwan et al. |
| 2006/0018973 | A1 | 1/2006 | Kim et al. |
| 2007/0071728 | A1 | 3/2007 | Ko et al. |
| 2007/0148161 | A1 | 6/2007 | Delmotte |
| 2008/0187591 | A1 | 8/2008 | Rhee et al. |
| 2009/0155342 | A1 | 6/2009 | Diegelmann et al. |
| 2010/0292624 | A1 | 11/2010 | Diegelmann et al. |
| 2010/0316739 | A1 | 12/2010 | Nisis |
| 2012/0207813 | A1 | 8/2012 | Rhee et al. |
| 2013/0129710 | A1 | 5/2013 | Nordhaus et al. |
| 2013/0224712 | A1 | 8/2013 | Day et al. |
| 2013/0287817 | A1 | 10/2013 | Drapeau et al. |
| 2013/0287837 | A1 | 10/2013 | MacPhee et al. |
| 2014/0072614 | A1 | 3/2014 | Rhee et al. |
| 2014/0187492 | A1 | 7/2014 | Falus et al. |
| 2014/0287061 | A1 | 9/2014 | Landolina |
| 2014/0314706 | A1 | 10/2014 | Diehn et al. |
| 2014/0369991 | A1 | 12/2014 | Schutte et al. |
| 2014/0378928 | A1 | 12/2014 | Hedrich et al. |
| 2015/0037774 | A1 | 2/2015 | Day et al. |

FOREIGN PATENT DOCUMENTS

| | | |
|---|---|---|
| EP | 2455109 A2 | 5/2012 |
| JP | 2000290633 A | 10/2000 |
| WO | 9617633 A1 | 6/1996 |
| WO | 9640174 A1 | 12/1996 |
| WO | 9808550 A1 | 3/1998 |
| WO | 9907417 A1 | 2/1999 |
| WO | 0076533 A1 | 12/2000 |
| WO | 02096978 A1 | 12/2002 |
| WO | 03035115 A2 | 5/2003 |
| WO | 2004028578 A1 | 4/2004 |
| WO | 2004032713 A2 | 4/2004 |

(Continued)

OTHER PUBLICATIONS

Calvo, Pilar, et al. "Novel hydrophilic chitosan-polyethylene oxide nanoparticles as protein carriers." Journal of Applied Polymer Science 63.1 (1997): 125-132. (Year: 1997).*
Piai, Juliana F., et al. "Kinetic study of Chondroitin Sulphate release from Chondroitin Sulphate/Chitosan complex hydrogel." Journal of Molecular Liquids 156.1 (2010): 28-32. (Year: 2010).*
International Search Report and Written Opinion of International Application No. PCT/US2014/038606, dated Oct. 10, 2016, 10 pages.
Zhao, Y et al. Pluronic-poly (acrylic acid)-cysteine/Pluronic L121 mixed micelles improve the oral bioavailability of paclitaxel. Drug development and industrial pharmacy. Nov. 1, 2014. vol. 40. No. 11; pp. 1483-1493.

(Continued)

*Primary Examiner* — Robert J Yamasaki
(74) *Attorney, Agent, or Firm* — Armstrong Teasdale LLP

(57) ABSTRACT

A method of inhibiting bleeding from an open surgical site includes mixing (i) a flowable gel solution comprising a biopolymer dissolved in a first solvent and (ii) a flowable hardener solution comprising a cross-linking agent dissolved in a second solvent to form a flowable hemostatic gel composition. The method also includes applying the flowable hemostatic gel composition to the open surgical site. The cross-linking agent links chains of the biopolymer together to form a solid hydrogel that inhibits bleeding from the surgical site.

9 Claims, 5 Drawing Sheets

(56) References Cited

FOREIGN PATENT DOCUMENTS

| WO | 2004112864 A2 | 12/2004 | |
| WO | 2006057011 A2 | 6/2006 | |
| WO | 2006088912 A2 | 8/2006 | |
| WO | WO-2007013717 A1 * | 2/2007 | ............... A21D 2/18 |
| WO | 2008016983 A2 | 2/2008 | |
| WO | 2008076407 A2 | 6/2008 | |
| WO | 2010057177 A2 | 5/2010 | |
| WO | 2010107794 A2 | 9/2010 | |
| WO | 2010134988 A1 | 11/2010 | |
| WO | WO-2011003155 A1 * | 1/2011 | ........... A61K 9/0024 |
| WO | 2011084326 A2 | 7/2011 | |
| WO | 2011124640 A1 | 10/2011 | |
| WO | 2011151384 A1 | 12/2011 | |
| WO | 2011151386 A1 | 12/2011 | |
| WO | 2011151400 A1 | 12/2011 | |
| WO | 2012030805 A2 | 3/2012 | |
| WO | 2012122044 A2 | 9/2012 | |
| WO | 2013003045 A2 | 1/2013 | |
| WO | 2013060769 A2 | 5/2013 | |
| WO | 2013096605 A1 | 6/2013 | |
| WO | 2013116633 A2 | 8/2013 | |
| WO | 2013126707 A1 | 8/2013 | |
| WO | 2013185776 A1 | 12/2013 | |
| WO | 2014142915 A1 | 9/2014 | |
| WO | 2014160136 A1 | 10/2014 | |

OTHER PUBLICATIONS

Sionkowska, A et al. Molecular interactions in collagen and chitosan blends. Biomaterials. Feb. 29, 2004. vol. 25. No. 5; pp. 795-801.

Gaffney, PJ et al. The International and "NIH" units forthrombin—how do they compare? Thrombosis and Flaemostasis. Sep. 1995 vol. 74. No. 3; abstract.

International Search Report and Written Opinion, dated Sep. 7, 2017, for co-pending International patent application No. PCT/US2017/038113.

Kang, Pei-Leun, et al. "Development and assessment of hemostasis chitosan dressings." Carbohydrate polymers 85.3 (2011): 565-570. (Year 2011).

* cited by examiner

FLOWABLE HEMOSTATIC GEL COMPOSITION AND ITS METHODS OF USE

BACKGROUND

The subject matter described herein relates generally to hemostatic compositions and, more particularly, to flowable hemostatic gel compositions configured for introduction to a surgical site.

It is necessary to inhibit bleeding from surgical incisions during and after a surgical procedure to minimize risk to a surgical subject. One known method to inhibit bleeding at a surgical site involves suturing the incision. However, many surgical procedures, such as but not limited to arteriotomies, involve internal incisions that are not easily accessible by suturing instruments. Other known methods to inhibit bleeding at a surgical site include an application of pressure manually and/or using a hemostatic device, and/or a use of absorbent materials, such as gauze and/or sponges. However, an effectiveness of such methods is limited for at least some incisions after the surgical procedure is complete. In addition, hemostatic gel compounds that include biopolymer materials such as chitosan and/or enzymatic clotting factors such as thrombin are known for treating skin wounds. However, an ability to deliver such known gel compounds to an internal surgical site is limited.

BRIEF SUMMARY

In one aspect, a method of inhibiting bleeding from an open surgical site is provided. The method includes mixing (i) a flowable gel solution comprising a biopolymer dissolved in a first solvent and (ii) a flowable hardener solution comprising a cross-linking agent dissolved in a second solvent to form a flowable hemostatic gel composition. The method also includes applying the flowable hemostatic gel composition to the open surgical site. The cross-linking agent links chains of the biopolymer together to form a solid hydrogel that inhibits bleeding from the surgical site.

In another aspect, a flowable hemostatic gel composition for use at an open surgical site is provided. The flowable hemostatic gel composition includes a mixture of (i) a flowable gel solution comprising a biopolymer dissolved in a first solvent and (ii) a flowable hardener solution comprising a cross-linking agent dissolved in a second solvent. The cross-linking agent is configured to link chains of the biopolymer together to form a solid hydrogel that inhibits bleeding from the surgical site.

DETAILED DESCRIPTION

Figure 1:
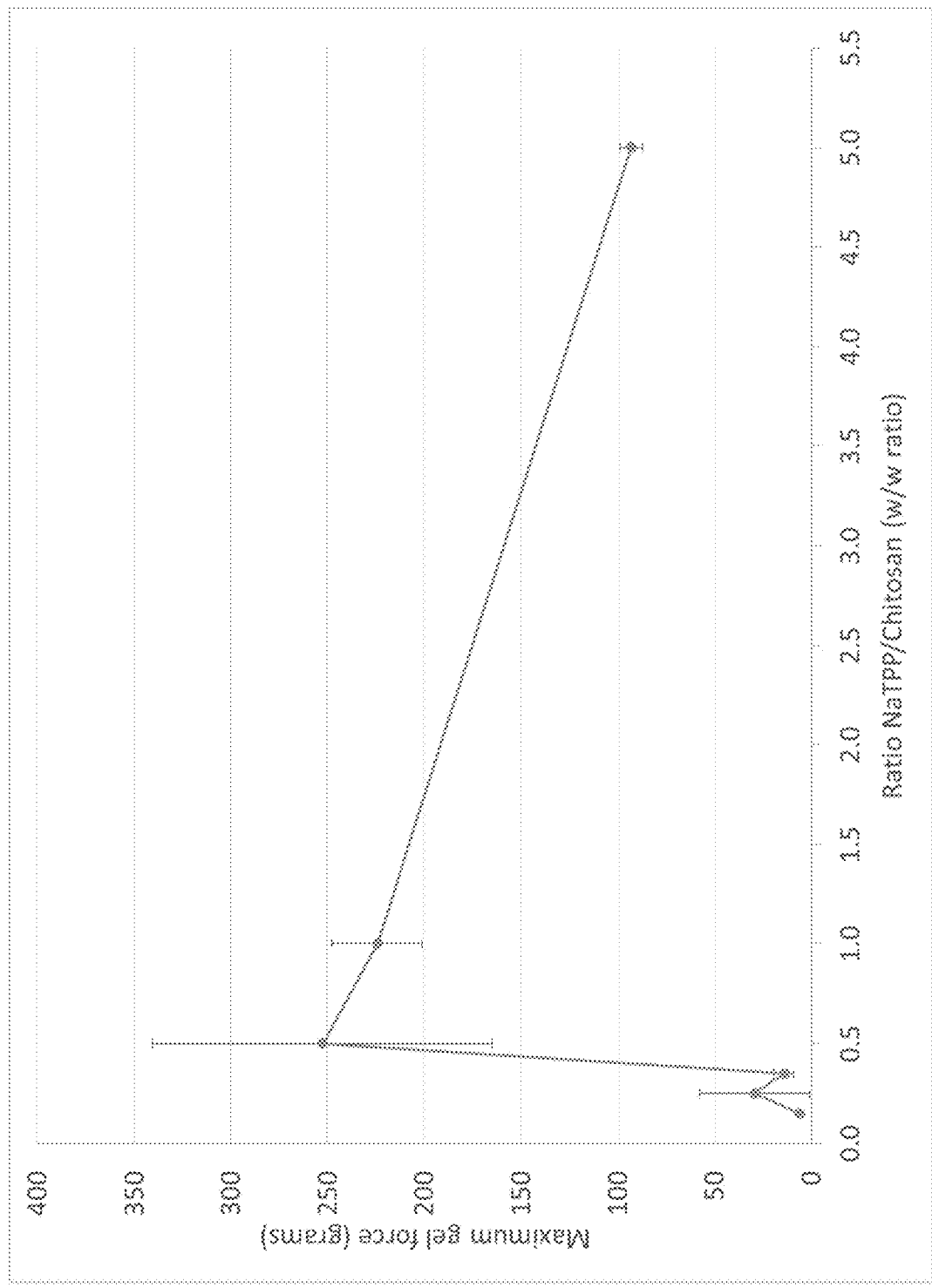
FIG. 1 is a graph summarizing a gel strength as a function of sodium tripolyphosphate:chitosan mass ratio for various hemostatic gel compositions.

The compositions and methods described herein relate to the inhibition of blood loss from a surgical incision of a subject and, more particularly, to a flowable hemostatic gel composition and methods of inhibiting blood flow from a surgical incision of a subject using the flowable hemostatic gel composition. The flowable hemostatic gel composition is formed from a gel solution containing a hemostatic biopolymer, mixed with a hardener solution containing a cross-linking agent. In some embodiments, the gel solution and the hardening solution are injected as separate solutions, while in other embodiments, the gel solution and the hardener solution are mixed just prior to and/or during flowable application. Upon flowable application to the incision site, such as but not limited to by injection, the flowable hemostatic gel composition rapidly cures in situ into a solid, ionic hemostatic hydrogel that inhibits blood loss from the incision. The solid hydrogel safely biodegrades in vivo, eliminating a need for any secondary removal process.

In some embodiments, the flowable hemostatic gel composition further includes at least one additional active agent such as, but not limited to, a clotting agent. For example, the at least one additional active agent is provided by pre-dissolving it into one of the gel solution and the hardener solution. After flowable introduction of the gel composition to the surgical site, the at least one incorporated active agent is released in active form to, for example, further facilitate inhibition of blood loss from the surgical site. In certain embodiments, the at least one active agent is selected to provide an alternative or additional benefit, such as to prevent infection or otherwise accelerate healing.

In some embodiments, the gel solution includes a biopolymer dissolved in a first solvent, and the hardener solution includes a cross-linking agent dissolved in a second solvent. For example, the gel solution includes chitosan dissolved in a lactic acid solution, and the hardener solution includes sodium tripolyphosphate (NaTPP) dissolved in water. In alternative embodiments, each of the biopolymer and first solvent of the gel solution, and the cross-linking agent and second solvent of the hardener solution, are selected to be any suitable materials, as described in detail below.

The flowable hemostatic gel composition is formulated to enable at least one property such as, but not limited to, viscosity or injectability of the gel solution, hardener solution, and/or mixture of the gel and hardener solutions; hemostatic properties of the gel composition; gel strength of the resulting solid hydrogel; time required for the mixed gel and hardener solutions to cure into the solid hydrogel; suitability of the flowable hemostatic gel composition for certain surgical methods and/or injection devices; and any other relevant property. The properties of the flowable hemostatic gel composition are governed by at least one of the composition of the gel and hardener solutions; the proportions of biopolymer and hardener combined to form the solid hydrogel; the inclusion of additional active agents in the flowable hemostatic gel composition; the method of introducing the flowable hemostatic gel composition to the incision site; and any other relevant property.

In certain embodiments, the biopolymer of the gel solution includes at least one polycationic polymer. Without being limited to any particular theory, the charges distributed within the polycationic polymer impart bioadhesive properties to enable the binding of a hemostatic gel containing the polycationic polymers to negatively charged surfaces including, but not limited to, biological tissues in the vicinity of a surgical site. Non-limiting examples of polycationic polymers suitable for inclusion in the gel solution include: chitosan, chitin, diethylaminoethyl-dextran, diethylaminoethyl-cellulose, diethylaminoethyl-agarose, diethylaminoethyl-alginate, any other polymer modified with a diethylaminoethyl group, any polymer containing a plurality of protonated amino groups, any polypeptide having an average residue isoelectric point above about 7, and any combination thereof.

In some embodiments, chitosan is selected as the polycationic polymer. Chitosan, as used herein, describes a naturally occurring linear polysaccharide composed of randomly distributed β-(1-4)-2-amino-2-D-glucosamine (deacetylated) and β-(1-4)-2-acetamido-2-D-glucosamine (acetylated) units. Chitosan may be derived from chitin, a naturally occurring polymer isolated from fungi, mollusks, or from the exoskeletons of arthropods (e.g., crustaceans and insects). Chitosan is produced by subjecting chitin to a process of alkaline deacetylation. As described more generally above, without being limited to any particular theory, positive charges along the backbone of chitosan cause it to interact electrostatically with negatively charged blood cells, thus creating a sticky interface between the chitosan within the hemostatic hydrogel composition and the surgical site. In addition, chitosan is also known to possess inherent antimicrobial properties.

In certain embodiments, the chitosan is produced using an alkaline deacetylation of chitin using a strong alkaline solution according to suitable methods. Typically, any chitin-based biopolymer with a degree of deacetylation greater than about 50% is referred to as chitosan. The degree of deacetylation of the chitosan may influence the characteristics of the hemostatic gel in which the chitosan is included. Non-limiting examples of characteristics of the hemostatic gel that may be influenced by the degree of acetylation of the chitosan include: gel strength, bioadhesive properties, and resistance to degradation in vivo at the surgical site.

The chitosan is provided in any suitable form including, but not limited to, powder, coarse ground flakes, or dissolved in a weak acid solvent. In some embodiments, the molecular weight of the chitosan is in a range from about 60 kDaltons to about 375 kDaltons (viscosity-average molecular weight $M_v$). Without being limited to any particular theory, the inclusion of chitosan of relatively higher molecular weight, such as at least 150 kDaltons, results in a solid hydrogel characterized by relatively slower degradation in vivo.

Chitosan is degraded in vivo by, for example, lysozyme, N-acetyl-o-glucosaminidase, and lipases, and the byproducts of chitosan degradation are saccharides and glucosamines that are gradually absorbed by the body. Therefore, no secondary process for removal from the body is required. Chitosan compositions having a 50% degree of deacetylation are highly degradable in vivo. As the degree of deacetylation increases, chitosan becomes increasingly resistant to degradation. Chitosan compositions having a degree of deacetylation that is higher than 95% degrade slowly over weeks or months. In certain embodiments, the degree of deacetylation of the chitosan in the gel solution is in a range from about 50% to about 100%. Moreover, in some embodiments, the degree of deacetylation is in a range from about 50% to about 80%. Moreover, in certain embodiments, the degree of deacetylation is in a range from about 65% to about 80%. In particular embodiments, the degree of deacetylation of the chitosan in the gel solution is about 75%.

In certain embodiments, the first solvent is selected to be a dilute acid solution, such as an aqueous solution that includes at least one of acetic, citric, oxalic, proprionic, ascorbic, hydrochloric, formic, lactic, or any other suitable organic or inorganic acid, in a range from about 0.1% to about 5% (v/v). For example, at least one polycationic polymer selected as the biopolymer is substantially insoluble in water and organic solvents, but is fairly soluble in dilute acid solutions. In some embodiments, the dilute acid is selected to influence at least one property of the gel solution, the flowable hemostatic gel composition, and/or the solid hydrogel, including, but not limited to, susceptibility to degradation in vivo, strength, and durability. Additionally or alternatively, a concentration of the dilute acid and/or a time period over which the chitosan is dissolved in the dilute acid is selected to influence at least one property of the gel solution, the flowable hemostatic gel composition, and/or the solid hydrogel, including, but not limited to, susceptibility to degradation in vivo, strength, and durability. As one example, the dilute acid is 1% L-lactic acid (v/v). As another example, the dilute acid is 1% acetic acid (v/v).

In some embodiments, the concentration of the biopolymer dissolved in the first solvent is selected to enable delivery of an effective amount of the biopolymer while maintaining a flowable viscosity of the gel solution. For example, the gel solution includes 1% w/v chitosan dissolved in 1% acetic acid, and has a viscosity in a range from about 200 centipoise (cP) to about 2000 cP. For another example, the gel solution includes 1% w/v chitosan of a relatively high molecular weight, as described above, dissolved in 1% acetic acid, and the gel solution has a viscosity in a range from about 800 cP to about 2000 cP. For another example, the gel solution includes within a range of 2-3% w/v chitosan of a relatively high molecular weight dissolved in 1% L-lactic acid, and the gel solution has a viscosity of about 1500 cP. In certain embodiments, a strength of the acid is selected to result in a pH of at least about 2. In particular embodiments, the strength of the acid is selected to result in a pH of at least about 4.

The cross-linking agent of the hardener solution is selected for its capability to cross-link the biopolymer of the gel solution upon mixture of the gel solution and hardener solution. For example, the cross-linking agent links chains of the biopolymer together to form a three-dimensional matrix of interconnected, linear, polymeric chains. In some embodiments, the linking of the chains of the biopolymer causes the flowable gel solution to rapidly cure into the solid hydrogel. In certain embodiments, the cross-linking agent is selected based upon at least one of the type of the polycationic polymer in the gel solution, the desired degree or extent of cross-linking, biocompatibility, and any other suitable factor. Non-limiting examples of suitable crosslinking agents include NaTPP, ethylene glycol diglycidyl ether, ethylene oxide, glutaraldehyde, epichlorohydrin, diisocyanate, calcium chloride, and genipin. For example, in certain embodiments, the cross-linking agent is selected to result in a cure time of less than about 10 seconds. For another example, in certain embodiments, the cross-linking agent is selected to result in a cure time of less than about one of 7, 6, 5, 4, 3, or 2 seconds.

In some embodiments, the second solvent of the hardener solution is selected to be water. For example, the cross-linking agent is fairly soluble in water. In certain embodiments, the concentration of the cross-linking agent dissolved in the second solvent is selected to enable delivery of an effective amount of the cross-linking agent while maintaining a flowable viscosity of the hardener solution.

For example, in certain embodiments, the polycationic polymer of the gel solution is chitosan and the cross-linking agent is NaTPP. In some such embodiments, the hardener solution includes NaTPP dissolved in water in a range from about 0.1% w/v to about 20% w/v. Moreover, in some such embodiments, the hardener solution includes NaTPP dissolved in water in a range from about 0.3% w/v to about 10% w/v. Moreover, in some such embodiments, the hardener solution includes NaTPP dissolved in water in a range from about 1% w/v to about 2% w/v. Moreover, in some such embodiments, the hardener solution includes NaTPP dissolved in water at about 2% w/v.

In some embodiments, a proportion of the cross-linking agent to the biopolymer in the flowable hemostatic gel composition is selected to produce a suitable gel strength of the solid hydrogel. For purposes of this disclosure, the gel strength of the solid hydrogel is defined as a maximum force (measured in grams) required to penetrate a 0.25 inch diameter ball bearing to a depth of 3.2 mm below the undeformed surface of the gel, as described in additional detail in Example 1 below. The gel strength is alternatively expressed in bloom units, defined as the maximum amount of force (in grams) required to penetrate a 1.2 inch diameter probe 4 mm below the undeformed surface of the gel. The bloom units are approximated using a linear conversion based on probe size.

For example, the biopolymer is chitosan and the cross-linking agent is NaTPP, the mass ratio of NaTPP to chitosan (NaTPP:chitosan, w:w) in the flowable hemostatic gel composition is in a range from about 0.5:1 to about 7:1, and the gel strength of the resulting solid hydrogel is in a range of about 50 g (approximately 240 bloom) to about 250 g (approximately 1200 bloom). For another example, the mass ratio (NaTPP:chitosan, w:w) is in a range from about 0.5:1 to about 5:1, and the gel strength of the resulting solid hydrogel is in a range of about 95 g (approximately 455 bloom) to about 250 g (approximately 1200 bloom). For another example, the mass ratio (NaTPP:chitosan, w:w) is in a range from about 0.5:1 to about 1:1, and the gel strength of the resulting solid hydrogel is in a range of about 220 g (approximately 1050 bloom) to about 250 g (approximately 1200 bloom). For another example, the mass ratio (NaTPP:chitosan, w:w) is about 0.5:1, and the gel strength of the resulting solid hydrogel is about 250 g (approximately 1200 bloom). For another example, the mass ratio (NaTPP:chitosan, w:w) is about 1:1, and the gel strength of the resulting solid hydrogel is about 220 g (approximately 1050 bloom).

In some embodiments, the flowable hemostatic gel composition further includes at least one additional active agent, such as, but not limited to, a clotting agent. Without being limited to any particular theory, the at least one additional active agent is incorporated into the hemostatic gel composition such that it is released from the resulting solid hydrogel in a predetermined release profile. Non-limiting examples of suitable additional active agents to be included in the hemostatic gel composition include clotting agents, antimicrobial agents such as antibiotics, anti-inflammatory agents such as non-steroidal anti-inflammatory drugs (NSAIDs), pain medications, tissue growth factors, and any combination thereof.

In certain embodiments, at least one additional active agent included in the hemostatic gel composition is selected to be a clotting agent. Non-limiting examples of clotting agents suitable for inclusion in the hemostatic gel composition include thrombin, fibrinogen, and any combination thereof. As used herein, "U" refers to an NIH-defined activity unit that corresponds to about 0.324 μg of enzymatically active thrombin. For example, at least one of the gel solution and the hardener solution includes an amount of thrombin in a range from about 0.1 U to about 200 U per gram of chitosan in the gel solution. For another example, at least one of the gel solution and the hardener solution includes an amount of thrombin in a range from about 2 U to about 160 U per gram of chitosan in the gel solution. In certain embodiments, a given amount of thrombin combined with chitosan results in greater thrombin enzymatic activity than does the given amount of thrombin in an absence of chitosan.

In some embodiments, higher amounts of chitosan result in increased activity of the thrombin. In certain embodiments, an amount of thrombin included in the flowable hemostatic gel composition is selected by a physician depending on factors associated with the patient.

The at least one additional active agent is incorporated into the flowable hemostatic gel composition in any suitable fashion. For example, at least one additional active agent is dissolved into the gel solution prior to mixture with the hardener solution. For another example, at least one additional active agent is dissolved into the hardener solution prior to mixture with the gel solution. For another example, at least one additional active agent is dissolved into both the gel solution and the hardener solution prior to mixture of the solutions.

Certain additional active agents, such as, but not limited to, thrombin, include protein-based enzymes subject to denaturing or damage that reduce a capability to perform enzymatic activity. In certain embodiments, at least one of the gel solution and the hardener solution is formulated to maintain the additional active agent in an enzymatically active state. For example, the ingredients of the gel solution and/or the hardener solution may be selected to maintain parameters within suitable ranges to facilitate maintaining the additional active agent in an enzymatically active state. Non-limiting examples of solution conditions selected to maintain the additional active agent in an enzymatically active condition include pH, ionic concentrations, temperature, and any other relevant solution parameter.

As one example, the gel solution includes 2% w/v chitosan dissolved in a 1% (v/v) aqueous solution of L-lactic acid, and the hardener solution includes 2% w/v NaTPP dissolved in water. Dissolving active thrombin in the gel solution and storing the thrombin-loaded gel solution at room temperature does not substantially reduce enzymatic activity of the thrombin, and mixing the thrombin-loaded gel solution with the hardener solution to form the flowable gel composition does not substantially reduce enzymatic activity of the thrombin. Similarly, dissolving active thrombin in the hardener solution, and mixing the result with the gel solution to form the flowable gel composition, does not substantially reduce enzymatic activity of the thrombin. Moreover, in each case, maintaining the resulting flowable gel composition at 37 degrees C. for a period of time ranging from about 30 minutes to several hours does not substantially reduce the enzymatic activity of the thrombin.

A predetermined release profile of each at least one additional active agent from the solid hydrogel formed from the flowable hemostatic gel composition is any suitable release profile. In certain embodiments, the predetermined release profile is influenced by at least one factor such as, but not limited to, an amount of the additional active agent loaded in the flowable hemostatic gel composition, a degree of cross-linking produced in the solid hydrogel, an amount of the additional active agent added to the gel solution as compared to an amount of the additional active agent added to the hardener solution, an incubation time of the additional active agent added to the gel solution, if any, with the biopolymer in the gel solution prior to mixture with the hardener solution, and the manner and/or timing of mixing the gel solution and the hardener solution. In some embodiments, the additional active agent is released from the solid hydrogel at a relatively steady (zero-order) rate. In other embodiments, the release profile is characterized by an initial release of the additional active agent at a relatively high rate, followed by an extended release at a relatively lower steady rate.

For example, the additional active agent is thrombin, and the release profile is selected based on at least one factor such as, but not limited to, the type and size of the surgical incision, the method of application of the flowable hemostatic gel composition, and/or the amount of gel applied to the surgical site. As another example, the gel solution includes 2% w/v chitosan dissolved in a 1% (v/v) aqueous solution of L-lactic acid, and thrombin is dissolved in the gel solution. The gel solution is incubated at room temperature for a period of time ranging from about 30 minutes to overnight prior to use in the hemostatic gel composition to enable the thrombin to form complexes with, or otherwise adhere to, the biopolymer in the gel solution, thereby forming a depot from which the thrombin may be released from the solid hydrogel according to the predefined release profile.

Figure 5:
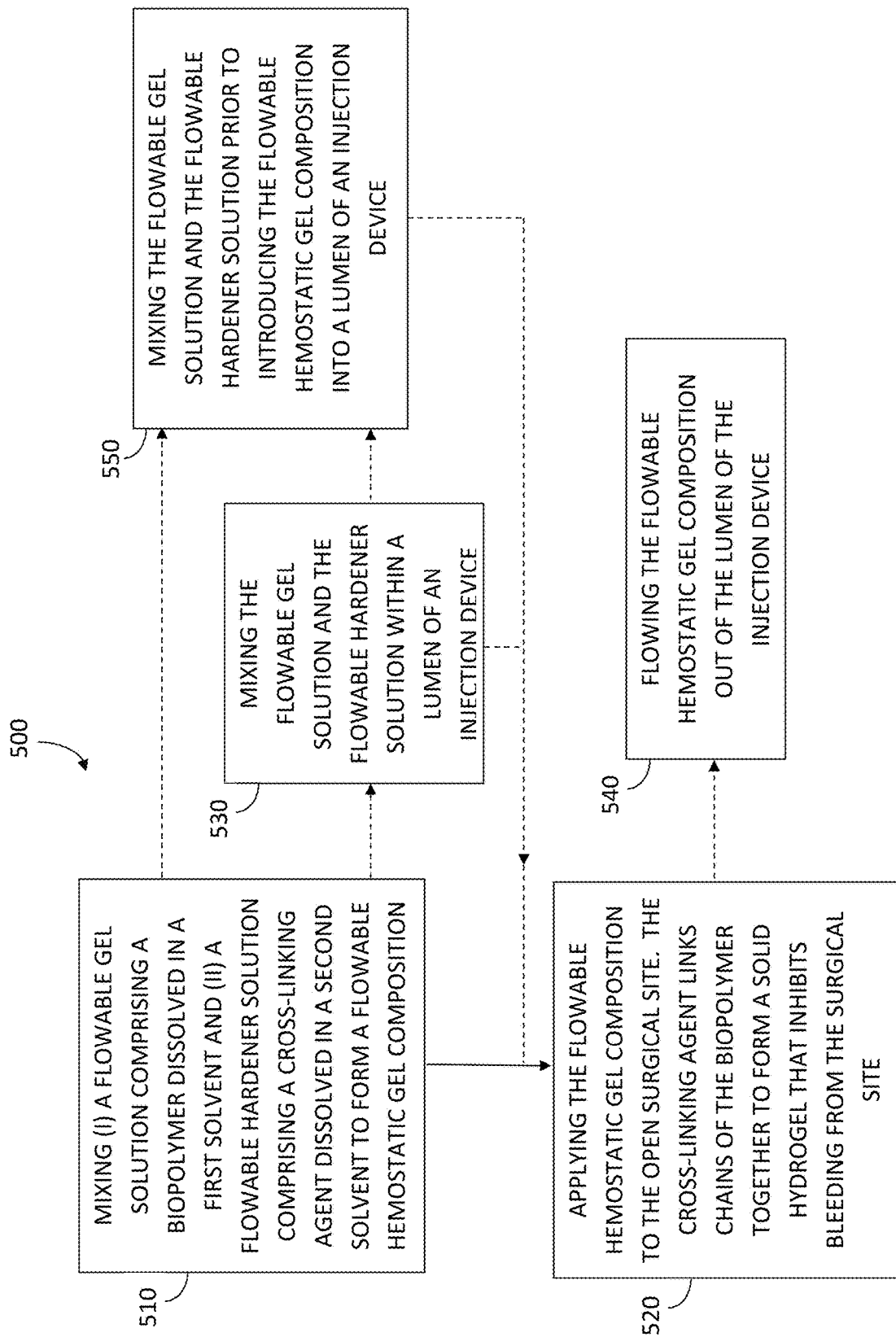
FIG. 5 is a flow diagram of an exemplary embodiment of a method of inhibiting bleeding from an open surgical site.

FIG. 5 is a flow diagram of an exemplary embodiment of a method 500 of inhibiting bleeding from an open surgical site. In the exemplary embodiment, method 500 includes mixing 510 (i) a flowable gel solution comprising a biopolymer dissolved in a first solvent and (ii) a flowable hardener solution comprising a cross-linking agent dissolved in a second solvent to form a flowable hemostatic gel composition. In the exemplary embodiment, method 500 also includes applying 520 the flowable hemostatic gel composition to the open surgical site. The cross-linking agent links chains of the biopolymer together to form a solid hydrogel that inhibits bleeding from the surgical site.

In certain embodiments, the step of mixing 510 the flowable gel solution and the flowable hardener solution includes mixing 530 the flowable gel solution and the flowable hardener solution within a lumen of an injection device, such as, but not limited to, a syringe, and the step of applying 520 the flowable hemostatic gel composition includes flowing 540 the flowable hemostatic gel composition out of the lumen of the injection device. For example, the surgical site includes an internal incision, and an outlet of the lumen of the injection device is positioned adjacent the internal incision to enable the flowable hemostatic gel composition to flow directly onto the surgical site. As described above, after the flowable hemostatic gel composition is applied, the cross-linking agent rapidly links chains of the biopolymer together to form a solid hydrogel that inhibits bleeding from the surgical site. Thus, an ability to apply the hemostatic gel composition in flowable form facilitates achieving hemostasis even for, but not only for, incisions that are difficult to access using traditional methods.

Additionally or alternatively, the step of mixing 510 the flowable gel solution and the flowable hardener solution further includes mixing 550 the flowable gel solution and the flowable hardener solution prior to introducing the flowable hemostatic gel composition into a lumen of an injection device, and prior to the step of flowing 540 the flowable hemostatic gel composition out of the lumen of the injection device. In certain embodiments, the method or sequence of introduction of the gel solution and the hardener solution to the surgical site influences one or more characteristics of the resulting hemostatic gel composition including, but not limited to, hardening time, gel strength, gel resistance to degradation, release rate of thrombin and/or other active agent included in the gel, and combinations thereof.

EXAMPLES

The examples illustrate various embodiments of the disclosure.

Example 1

Mechanical Strength of Solid Hemostatic Gel Formed from the Flowable Hemostatic Gel Composition To evaluate the gel strength of various compositions of hemostatic gel as described herein above, the following experiments were conducted.

Chitosan (Aldrich Cat#419419, Sigma-Aldrich, St. Louis, Mo.) was dissolved at 2% w/v in a first solvent solution of 1% v/v L-lactic acid to form a gel solution. Sodium tripolyphosphate (NaTPP, Aldrich Cat#238503) was dissolved in a second solvent of de-ionized water (DiH$_2$O) to form a series of hardener solutions in the respective amounts of 0.3% w/v, 0.5% w/v, 0.7% w/v, 1% w/v, 2% w/v, and 10% w/v NaTPP.

To form the solid hydrogel samples, 0.5 ml of gel solution and 0.5 ml of hardener solution at the various concentrations (see Table 1) were added by pipette to a two-mL microfuge tube, such that a total volume of the flowable hemostatic gel composition was constant. Each sample was mixed and equilibrated overnight in a 100 RPM/37° C. shaking incubator.

Mechanical testing was performed on each resulting solid hydrogel sample using a TA.XTplus analyzer. A 0.25-inch steel ball was forced into the solid hydrogel at a crosshead speed of 1 mm/sec to a depth of 3.2 mm, in order to immerse the steel ball up to the ball's midpoint, and testing was initiated at 2 g of resistance force. The maximum resistance force encountered during the test was recorded to determine each sample's gel strength. Triplicate mechanical testing was performed for each NaTPP concentration.

Table 1 below summarizes the results of the mechanical testing. FIG. 1 is a graph summarizing the maximum gel force obtained for each sample as a function of the NaTPP:chitosan mass ratio. The gel strength was observed to increase as the NaTPP content of the gel samples increased, up to a maximum gel strength at a NaTPP:chitosan mass ratio of 0.5:1. NaTPP:chitosan mass ratios above 0.5 resulted in successively decreasing gel strengths, although the gel strengths remained substantial.

TABLE 1

Mechanical Strength of Hemostatic Gel Compositions.

| Gel Composition (all quantities in % w/v) | NaTPP/Chitosan mass ratio (w/w) | Max Force (g) mean ± SD (N = 3) |
|---|---|---|
| 0.5 ml of 2% CGF plus 0.5 ml 0.3% NaTPP | 0.2 | 6.0 ± 1.3 |
| 0.5 ml of 2% CGF plus 0.5 ml 0.5% NaTPP | 0.3 | 29.3 ± 28.4 |
| 0.5 ml of 2% CGF plus 0.5 ml 0.7% NaTPP | 0.4 | 14.1 ± 5.0 |
| 0.5 ml of 2% CGF plus 0.5 ml 1% NaTPP | 0.5 | 252.7 ± 87.6 |

TABLE 1-continued

Mechanical Strength of Hemostatic Gel Compositions.

| Gel Composition (all quantities in % w/v) | NaTPP/ Chitosan mass ratio (w/w) | Max Force (g) mean ± SD (N = 3) |
|---|---|---|
| 0.5 ml of 2% CGF plus 0.5 ml 2% NaTPP | 1.0 | 224.4 ± 23.3 |
| 0.5 ml of 2% CGF plus 0.5 ml 10% NaTPP | 5.0 | 93.2 ± 5.8 |

The results of these experiments demonstrated the sensitivity of the gel strength to NaTPP:chitosan mass ratio of the gel composition. Further, the results of these experiments indicated that the highest gel strengths were achieved at NaTPP:chitosan mass ratios ranging from about 0.5:1 to about 1:1.

Example 2

Validation of Determination of Additional Active Agent Enzymatic Activity

The following experiments were conducted to ensure accurate determinations of enzymatic activity of an additional active agent, thrombin, loaded into the gel solution and, alternatively or additionally, into the hardener solution.

To determine the presence of enzymatically active thrombin, a highly specific chromogenic thrombin substrate (Aldrich Cat# T3068, Sigma-Aldrich, St. Louis, Mo.) was utilized. This thrombin substrate includes a cleavably linked beta-Ala-Gly-Arg para-nitroanilide. Upon contact with enzymatically active thrombin, release of the p-nitroanilide from the peptide linkage generates a UV absorbance around 405 nm.

To ensure minimal exposure to other enzymes or biologically active materials which may cause either substrate cleavage or thrombin degradation, the solution used for dissolving all enzymes and substrates was phosphate buffered saline (PBS) (10× concentrated, Aldrich Cat#P5493, Sigma-Aldrich, St. Louis, Mo.), aseptically diluted to 1× using BPC grade water (Aldrich Cat#W3513, Sigma-Aldrich, St. Louis, Mo.). The PBS solution was 0.2 µm filtered (Nalgene Cat#190-2520, Thermo Fisher Scientific Inc., USA) prior to use to maintain sterility. The solutions were produced in a labconco purifier class II hood that had been sprayed down with 70% ethanol solution and UV light exposed for 20 minutes prior to initiating work to reduce bacterial contamination.

Thrombin from human plasma lyophilized powder (Aldrich Cat# T8885, Sigma-Aldrich, St. Louis, Mo.) was diluted in 5 ml of PBS thus forming a 3.2 U/ml thrombin solution. The thrombin substrate was also dissolved in 5 ml of PBS forming a 5 mg/ml substrate solution.

A positive control (thrombin-positive) sample was generated by combining 0.1 ml of the substrate solution along with 0.1 ml of the thrombin solution and 1.8 ml of PBS. A negative control (thrombin-negative) sample was generated by combining 0.1 ml of the substrate solution in 1.9 ml of PBS. Both samples were incubated at 37° C. overnight. The next day the positive sample was visibly observed to be yellow in color while the negative sample was still clear.

Figure 2:
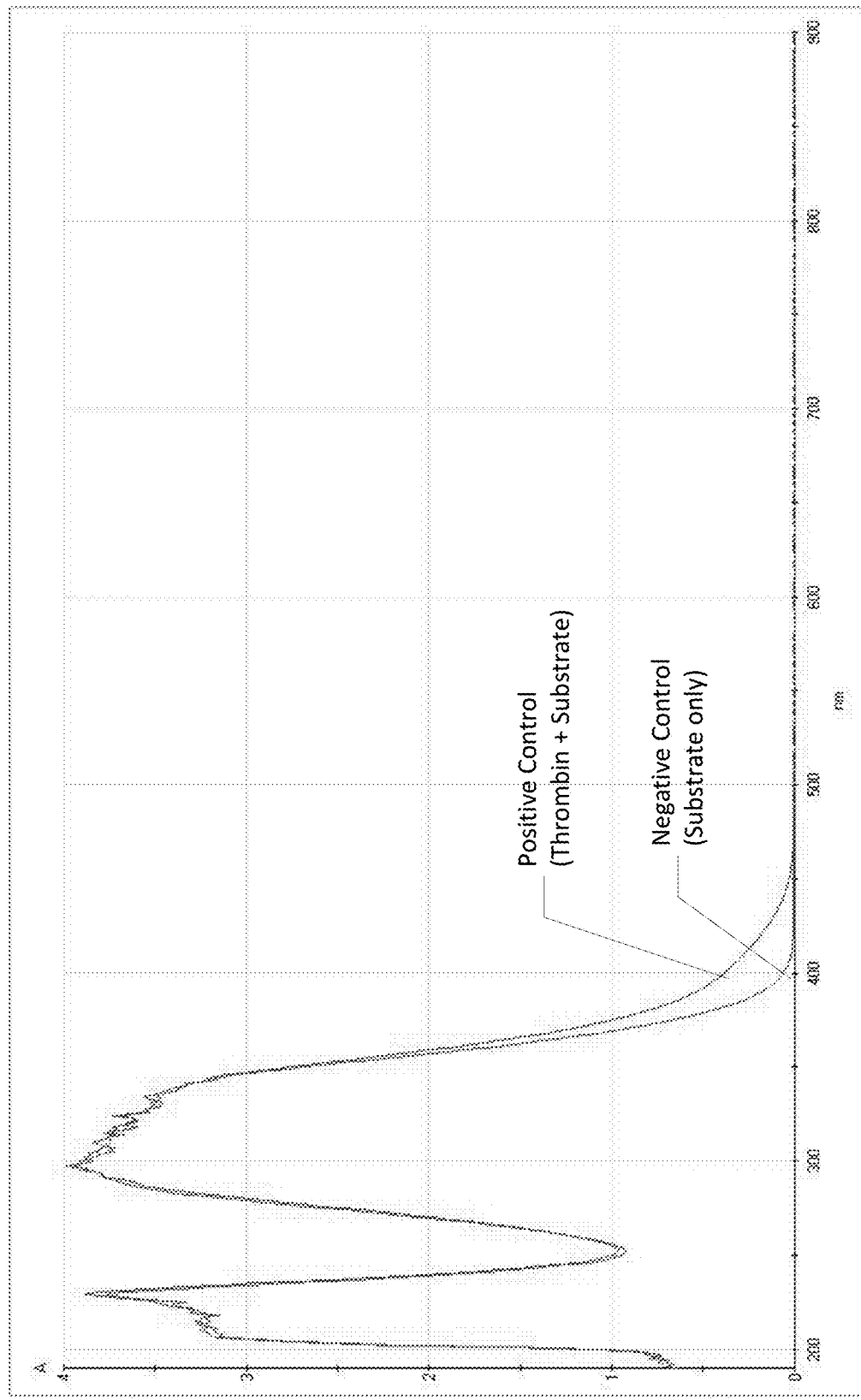
FIG. 2 is a graph summarizing absorbance spectra of a buffered positive control sample including thrombin and a substrate, and a buffered negative control sample including the substrate only, using the buffer solution alone as a blank.
Figure 3:
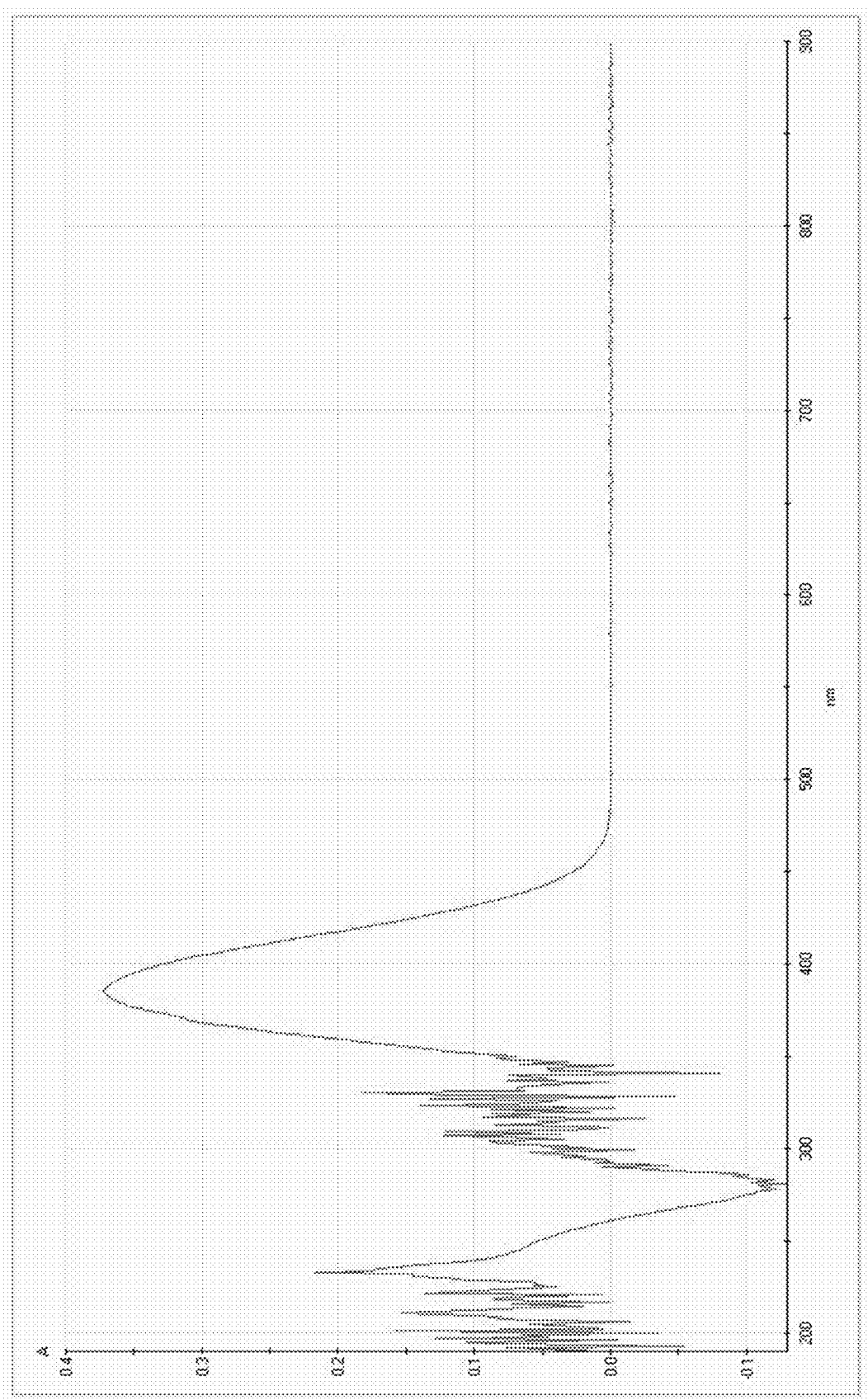
FIG. 3 is a graph summarizing absorbance spectra of the buffered positive control sample of FIG. 2 using the buffered negative control sample of FIG. 2 as a blank.

The positive control sample and the negative control sample were subjected to absorption spectroscopic analysis in the UV and visible wavelength ranges. FIG. 2 is a graph summarizing the UV/Vis absorption spectra of the positive and negative control samples scanned against a blank of 2 ml of PBS. To focus on the difference between the positive and negative control samples (i.e. the signal produced by the addition of thrombin), a UV/Vis absorption spectrum of the positive control samples was obtained using the negative control sample as the blank; the obtained spectrum is summarized in FIG. 3. Referring to FIG. 2 and FIG. 3, the peak difference in absorbance between the positive and negative control samples was observed at 385 nm.

The results of this experiment validated the assay for enzymatically active thrombin using the chromogenic thrombin substrate described above. The assay exhibited peak sensitivity at an assay wavelength of 385 nm. Based on this finding, an assay wavelength of 385 nm, as well as an assay wavelength of 405 nm suggested by the manufacturer, were selected for use in subsequent thrombin release experiments described below. Further, due to the relatively low UV absorption exhibited in the results of this experiment, the amount of thrombin substrate solution was doubled to 0.2 mL for use in subsequent thrombin release experiments.

Example 3

Preservation of Enzymatic Activity of Additional Active Agent

The following experiments were conducted to ensure that an enzyme-based additional active agent, thrombin, loaded into the gel solution and, alternatively or additionally, into the hardener solution, retained its enzymatic activity after combination and formation of the solid hydrogel.

A series of samples were produced for the various compositions as summarized in Table 2 below. Negative and positive control samples similar to those described in Example 2 were produced, as well as various combinations of the gel solution and hardener solution described in Example 1 plus the thrombin solution described in Example 2. Referring to Table 2, samples were produced containing 2% NaTPP only, 2% chitosan only, and thrombin only. Additional samples were produced in which: a) thrombin was added to the NaTPP hardener solution, to which mixture the chitosan gel solution was added subsequently, and b) thrombin was added to the chitosan gel solution, to which mixture the NaTPP hardener solution was added subsequently. All samples were mixed in 2 ml plastic vials.

After mixing at 37° C. and 100 RPM for 5 minutes, 0.2 ml aliquots of the supernatant (excluding solid gel if formed) from each sample vial was pulled and mixed with 0.2 ml of the substrate solution described in Example 2, along with 1.6 ml of PBS. Additional samples in which thrombin was added to the chitosan gel solution, to which mixture the NaTPP hardener solution was added subsequently, were further incubated at 37° C. for 30 minutes and for 1 hour prior to pulling supernatant aliquots for subsequent analysis. The mixtures of supernatant aliquots and substrate solution were then incubated overnight at 37° C. and subsequently analyzed to assess the UV absorbance of each mixture at wavelengths of 385 nm and 405 nm as compared to a PBS blank in order to assess the enzymatically active thrombin content of each aliquot.

The results of the UV absorbance analysis are summarized in Table 2 below. Referring to Table 2, the sample absorbance at a wavelength of 405 nm was determined to be more discriminatory for enzymatically active thrombin content than the corresponding absorbance at a wavelength of 385 nm. The negative control sample had very low absorbance (0.071) and there was relatively low indication of interference from chitosan alone, NaTPP alone, or the mixture of chitosan and NaTPP (absorbance <0.2 for all corresponding samples) which indicates that the substrate solution is suitably selective so as to be cleaved by enzymatically active thrombin, rather than by other non-specific agents such as pH changes or ionicity. Thrombin activity was observed in the sample of thrombin mixed with PBS but, interestingly, the measured thrombin activity was relatively low as compared to the thrombin-loaded chitosan gel solution samples. No significant difference in thrombin activity was observed between the sample in which thrombin was mixed first with the chitosan gel solution and the sample in which thrombin was mixed first with the NaTPP hardener solution, indicating that neither solution denatures the thrombin enzyme. Incubating the resulting thrombin-loaded solid hydrogel at 37° C. for longer periods of time did not decrease enzymatic activity, and indeed appeared to enhance enzymatic activity slightly. It should be noted that the results described below are relative measures of enzymatic activity among samples, rather than exact quantifications of absolute enzymatic activity levels.

TABLE 2

UV/Vis Absorbance of Thrombin Released from Hemostatic Gel Compositions.

| Sample Description | Absorbance (385 nm) | Absorbance (405 nm) |
|---|---|---|
| Negative control (0.2 ml of substrate and 1.8 ml of PBS) | 0.603 | 0.071 |
| Positive control (0.2 ml of substrate, 0.2 ml of thrombin and 1.6 ml of PBS) | 2.269 | 1.404 |
| Sample 0.5 ml 2% NaTPP + 0.5 ml PBS | 0.666 | 0.106 |
| Sample 0.5 ml 2% Chitosan + 0.5 ml PBS | 0.650 | 0.072 |
| Sample 0.5 ml 2% NaTPP + 0.5 ml 2% Chitosan | 0.677 | 0.114 |
| Sample 0.2 ml Thrombin + 1 ml PBS | 0.913 | 0.314 |
| Sample 0.2 ml Thrombin + 0.5 ml 2% Chitosan (mixed first), then added 0.5 ml 2% NaTPP | 1.446 | 0.737 |
| Sample 0.2 ml Thrombin + 0.5 ml 2% NaTPP (mixed first), then added 0.5 ml 2% Chitosan | 1.513 | 0.797 |
| Sample 0.2 ml Thrombin + 0.5 ml 2% Chitosan (mixed first), then added 0.5 ml 2% NaTPP gel incubated 37° C./100 RPM for 30 min prior to sampling | 1.813 | 1.036 |
| Sample 0.2 ml Thrombin + 0.5 ml 2% Chitosan (mixed first), then added 0.5 ml 2% NaTPP gel incubated 37° C./100 RPM for 1 hour prior to sampling | 1.800 | 1.024 |

The results of the experiment demonstrated that the solid hydrogel formed from the flowable hemostatic gel composition including an enzyme-based additional active agent described herein released the chitosan in an enzymatically active form. Further, the release of the enzymatically active agent was relatively insensitive to various factors in the production of the flowable hemostatic gel composition, including order of mixing ingredients and incubation time used to form the gel.

Example 4

Verification of Stable Storage and Differential Loading Ability of Enzyme-Based Additional Active Agent The following experiments were conducted to verify stable storage of the flowable hemostatic gel composition with an added enzyme-based additional active agent, and to validate an ability to tailor the loading of the enzyme-based additional active agent for therapeutic effect.

A series of mixtures were formed from 2% w/v chitosan gel solution, as described in Example 1, combined with varying volumes of 3.2 U/ml thrombin solution, as described in Example 2, with gentle shaking at room temperature overnight to fully incorporate the thrombin into the chitosan gel solution. For comparison, the mixture of 0.2 ml thrombin and 0.5 ml of 2% w/v chitosan solution formed previously in Example 3 also was obtained for use in these experiments to further assess the effect of storage time on thrombin activity. The thrombin content of each solution is summarized in Table 3 below.

TABLE 3

Chitosan-Thrombin Mixtures Used in Gel Compositions.

| Thrombin Content (% v/v) | Mixture Method (note thrombin solution is 3.2 U/ml) | Theoretical Units Thrombin/Gram Chitosan (U/g) |
|---|---|---|
| 1% | 0.01 ml thrombin + 0.99 ml 2% chitosan | 2 |
| 5% | 0.05 ml thrombin + 0.95 ml 2% chitosan | 8 |
| 10% | 0.1 ml thrombin + 0.9 ml 2% chitosan | 18 |
| 25% | 0.25 ml thrombin + 0.75 ml 2% chitosan | 53 |
| 50% | 0.5 ml thrombin + 0.5 ml 2% chitosan | 160 |
| 0.2 ml Thrombin + 0.5 ml 2% Chitosan (earlier test, included for reference) | See Example 3 | 64 |

After mixing overnight, each thrombin/chitosan solution was split into two 0.5 ml aliquots. The first aliquot from each solution was put in the bottom of a vial and 0.5 ml of 2% NaTPP hardener solution was added on top to form "chitosan first" flowable gel compositions. The second aliquot from each solution was pipetted into a vial which already contained 0.5 ml of 2% NaTPP hardener solution to form "NaTPP first" flowable gel compositions. These flowable gel compositions were incubated at 37° C./100 RPM for 2 hours, and then 0.2 ml of supernatant was pulled from each sample and tested for thrombin activity as described in Example 3. The samples tested for thrombin activity are summarized in Table 4 below.

TABLE 4

Thrombin Release from Thrombin Loaded Gel Compositions

| Sample Description | Absorbance at 385 nm | Absorbance at 405 nm |
|---|---|---|
| Negative control (0.2 ml of substrate and 1.8 ml of PBS) | 0.624 | 0.073 |
| Positive control (0.2 ml of substrate, 0.2 ml of thrombin and 1.6 ml of PBS) | 2.261 | 1.394 |
| Chitosan plus thrombin (2 U/g) chitosan first | 0.663 | 0.095 |
| Chitosan plus thrombin (8 U/g) chitosan first | 0.669 | 0.1 |
| Chitosan plus thrombin (18 U/g) chitosan first | 0.695 | 0.111 |
| Chitosan plus thrombin (53 U/g) chitosan first | 0.955 | 0.332 |
| Chitosan plus thrombin (160 U/g) chitosan first | 1.592 | 0.85 |
| Chitosan plus thrombin (2 U/g) NaTPP first | 0.637 | 0.084 |
| Chitosan plus thrombin (8 U/g) NaTPP first | 0.685 | 0.111 |
| Chitosan plus thrombin (18 U/g) NaTPP first | 0.706 | 0.128 |
| Chitosan plus thrombin (53 U/g) NaTPP first | 0.824 | 0.224 |
| Chitosan plus thrombin (160 U/g) NaTPP first | 1.029 | 0.381 |

Figure 4:
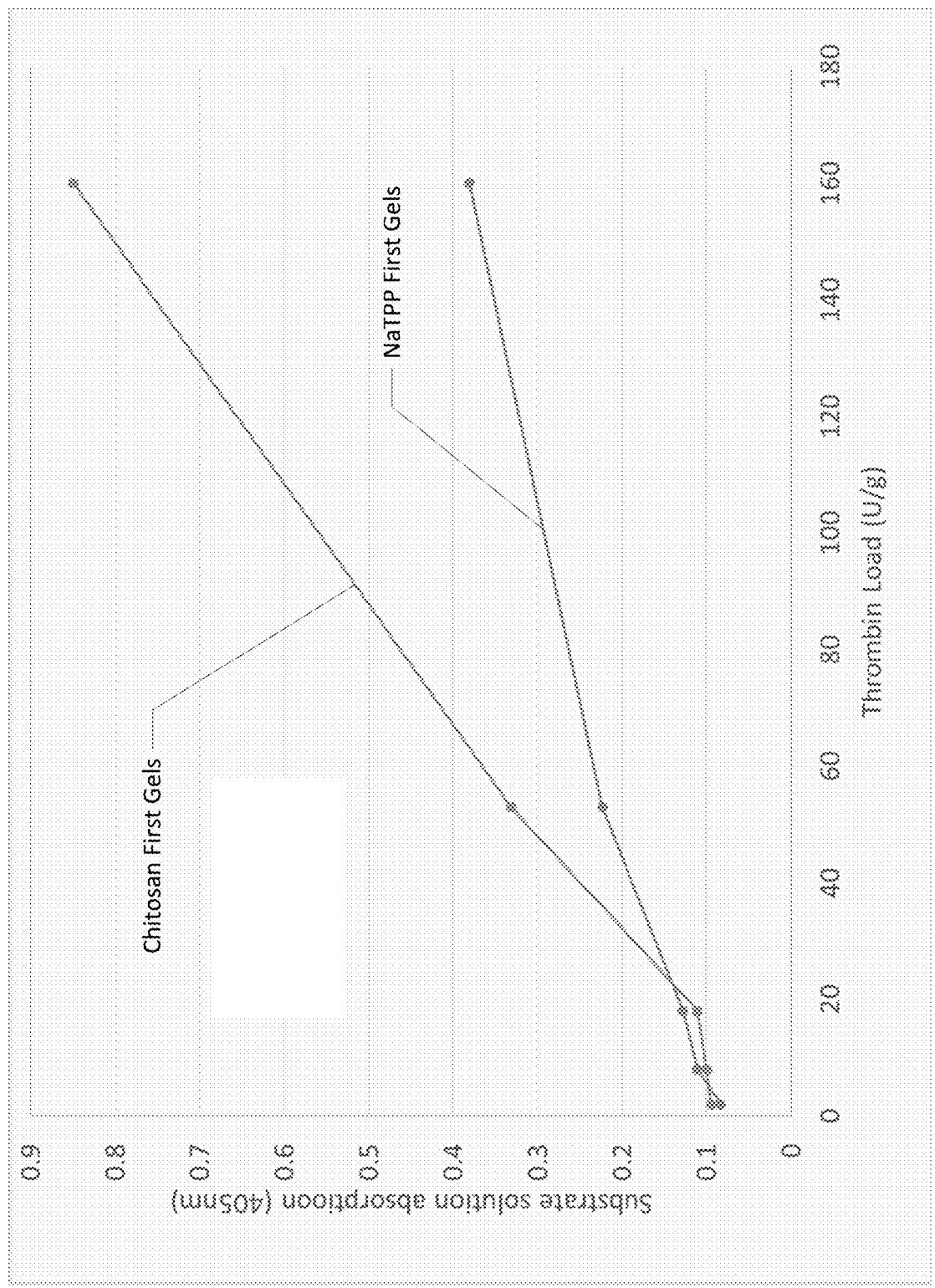
FIG. 4 is a graph summarizing a release of enzymatically active thrombin from a hemostatic gel composition as a function of thrombin loading of the hemostatic gel composition.

FIG. 4 summarizes the relative changes in thrombin activity, measured as absorbance at 405 nm, as a function of thrombin loading for the gel compositions tested. These relative curves for the chitosan-first compositions and the NaTPP-first compositions generally indicate a dose-dependent relationship with respect to thrombin loading of the gel solution, in which higher quantities of thrombin cleave more of the substrate used to assay thrombin activity. Note that the thrombin content of the test solutions analyzed in this experiment ranged from 0.0032 U to 0.32 U, whereas the thrombin content of the positive control from Ex. 3 contained 0.64 U.

The results of this experiment demonstrate a dose-dependent relationship of release of the additional active agent from the solid hydrogel with respect to the amount of additional active agent loaded into each flowable hemostatic gel composition.

Exemplary embodiments of the hemostatic gel composition and methods of use are described above in detail. The methods and compositions are not limited to the specific embodiments described herein, but rather, operations of the methods and components of the systems may be utilized independently and separately from other operations and/or components described herein. For example, the methods and compositions described herein may have other industrial and/or consumer applications and are not limited to practice in medical applications as described herein. Rather, one or more embodiments may be implemented and utilized in connection with other industries.

As used herein, an element or step recited in the singular and proceeded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A flowable hemostatic gel composition for use at an open surgical site, the flowable hemostatic gel composition consisting of:
   (i) a solvent comprising water;
   (ii) an acid in a range from about 0.05% to about 2.5% (v/v) of the solvent; and
   (iii) a solute consisting of chitosan and sodium tripolyphosphate provided in proportion to the chitosan in a ratio from about 0.5:1 to about 7:1 (w/w).

2. The flowable hemostatic gel composition of claim 1, wherein the cross-linking agent is provided in proportion to the biopolymer in a ratio such that a gel strength of a solid hydrogel formed at room temperature from the flowable hemostatic gel composition is in a range of about 50 g to about 250 g, wherein the gel strength is a maximum resistance force encountered by a 0.25-inch steel ball moved into the solid hydrogel at a speed of 1 mm/sec to a depth of 3.2 mm.

3. The flowable hemostatic gel composition of claim 1, wherein the chitosan has a degree of deacetylation in a range from about 50% to about 80%.

4. The flowable hemostatic gel composition of claim 1, wherein the acid comprises lactic acid.

5. The flowable hemostatic gel composition of claim 1, wherein the acid comprises acetic acid.

6. The flowable hemostatic gel composition of claim 1, wherein the sodium tripolyphosphate is provided in proportion to the chitosan in a ratio from about 0.5:1 to about 1:1.

7. A flowable hemostatic gel composition for use at an open surgical site, the flowable hemostatic gel composition consisting of:
   (i) a solvent comprising water;
   (ii) an acid in a range from about 0.05% to about 2.5% (v/v) of the solvent;
   (iii) a solute consisting of chitosan, sodium tripolyphosphate provided in proportion to the chitosan in a ratio from about 0.5:1 to about 7:1 (w/w), and phosphate buffered saline; and
   (iv) at least one clotting factor releasable in active form from a solid hydrogel formed in vivo from the flowable hemostatic gel composition.

8. The flowable hemostatic gel composition of claim 7, wherein the flowable hemostatic gel composition is formulated to maintain the at least one clotting factor in an enzymatically active state.

9. The flowable hemostatic gel composition of claim 7, wherein the at least one clotting factor includes at least one of thrombin and fibrinogen.

* * * * *